United States Patent [19]
Gutcheck et al.

[11] Patent Number: 5,311,013
[45] Date of Patent: May 10, 1994

[54] OPTICAL FIBER DISTRIBUTION SYSTEM FOR AN OPTICAL FIBER SENSOR IN A LUMINESCENT SENSOR SYSTEM

[75] Inventors: Robert A. Gutcheck, Bothell; John M. Lindberg, Redmond, both of Wash.; Gerald G. Vurek, Mountain View, Calif.

[73] Assignee: Abbott Laboratories, Abbott Park, Ill.

[21] Appl. No.: 961,559

[22] Filed: Oct. 15, 1992

[51] Int. Cl.$^5$ .................. A61B 5/00; G01N 33/48; H01J 5/16
[52] U.S. Cl. ................. 250/227.23; 356/41; 128/634
[58] Field of Search ............ 250/227.23, 226, 227.21; 356/39–41; 385/12; 128/633, 634

[56] References Cited

U.S. PATENT DOCUMENTS

| | | | |
|---|---|---|---|
| 4,644,154 | 2/1987 | Brogardh et al. | 250/227.23 |
| 4,760,250 | 7/1988 | Loeppert | 250/227.23 |
| 4,803,361 | 2/1989 | Aiki et al. | 250/227.24 |
| 4,907,857 | 3/1990 | Giuliani et al. | 250/227.23 |
| 4,989,935 | 2/1992 | Stein | 250/227.23 |
| 5,047,627 | 9/1991 | Yim et al. | 356/41 |
| 5,119,463 | 6/1992 | Vurek et al. | 385/12 |
| 5,142,155 | 8/1992 | Mauze et al. | 250/227.23 |
| 5,173,432 | 12/1992 | Lefkowitz et al. | 356/41 |
| 5,176,882 | 1/1993 | Gray et al. | 385/12 |

*Primary Examiner*—Michael Messinger
*Attorney, Agent, or Firm*—Harry G. Thibault; Robert E. Wexler

[57] ABSTRACT

An optical distribution system incorporating an improved luminescent based optical fiber sensor incorporating a signal generating component for generating a first optical signal, a signal separating component for delivering said first optical signal to the sensor, delivering said second returned optical signal to an associated signal detector, and including signal interference means to separate said first and second signals and minimize cross-talk therebetween. A sensor optical fiber connects a sensor tip to the signal separating component. The signal detector receives a returned signal from the signal separating component and transmits it to a signal-measuring component of the distribution system.

14 Claims, 4 Drawing Sheets

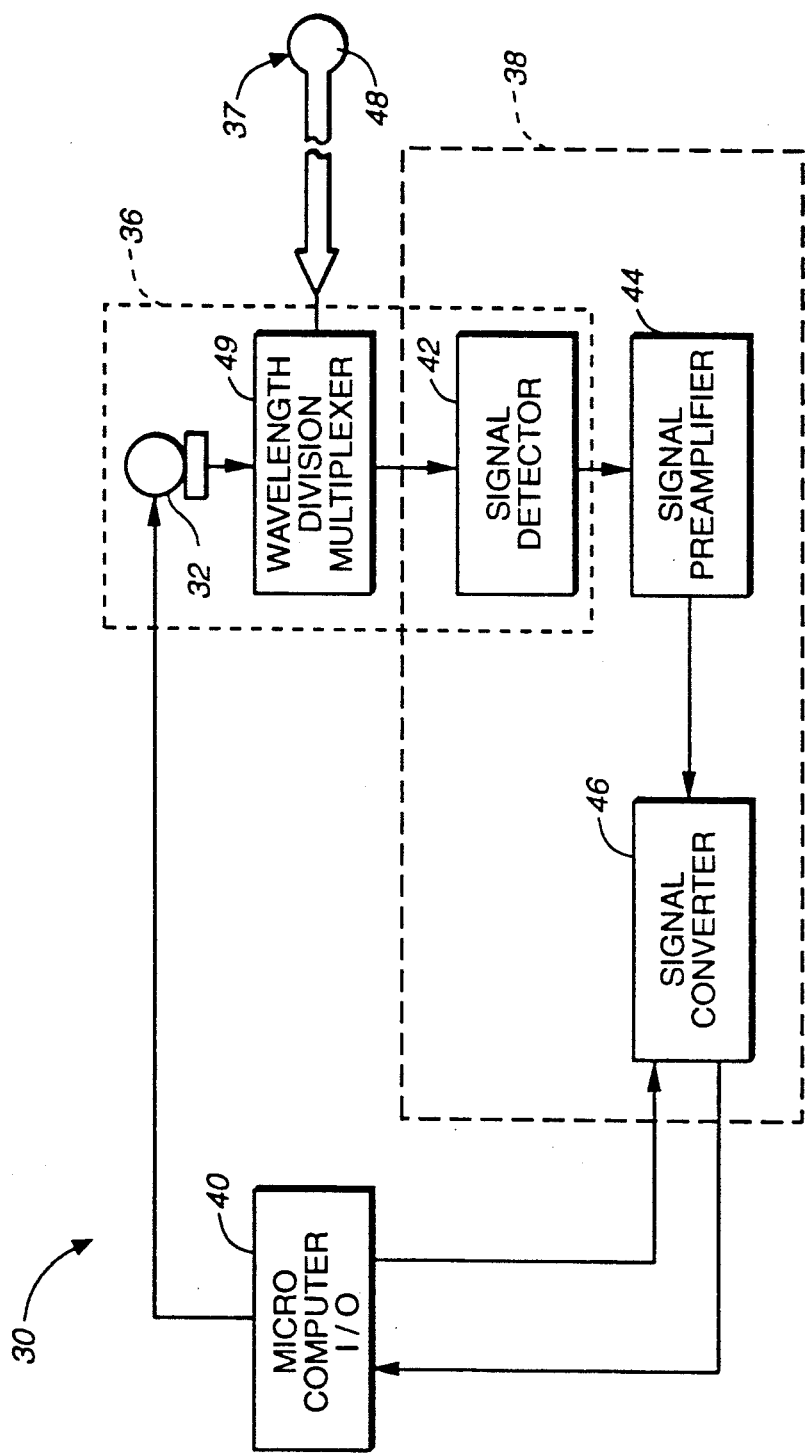
FIG._1

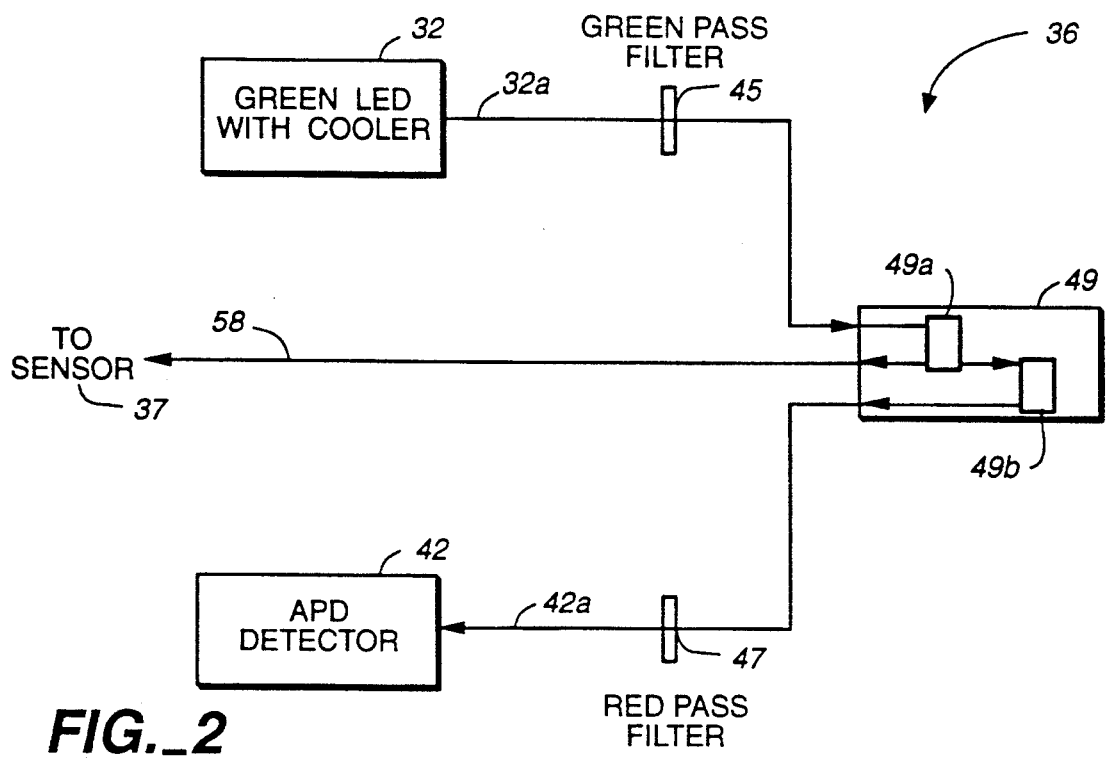
FIG._2
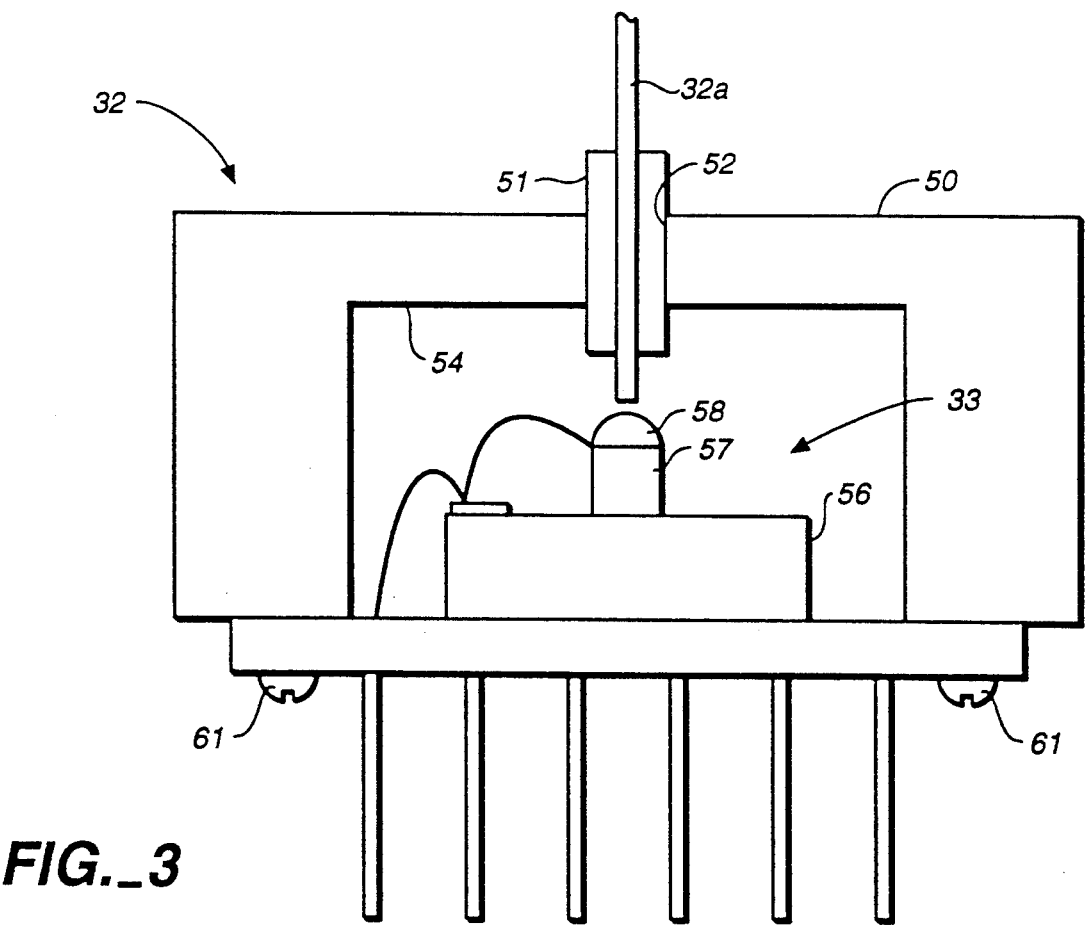
FIG._3

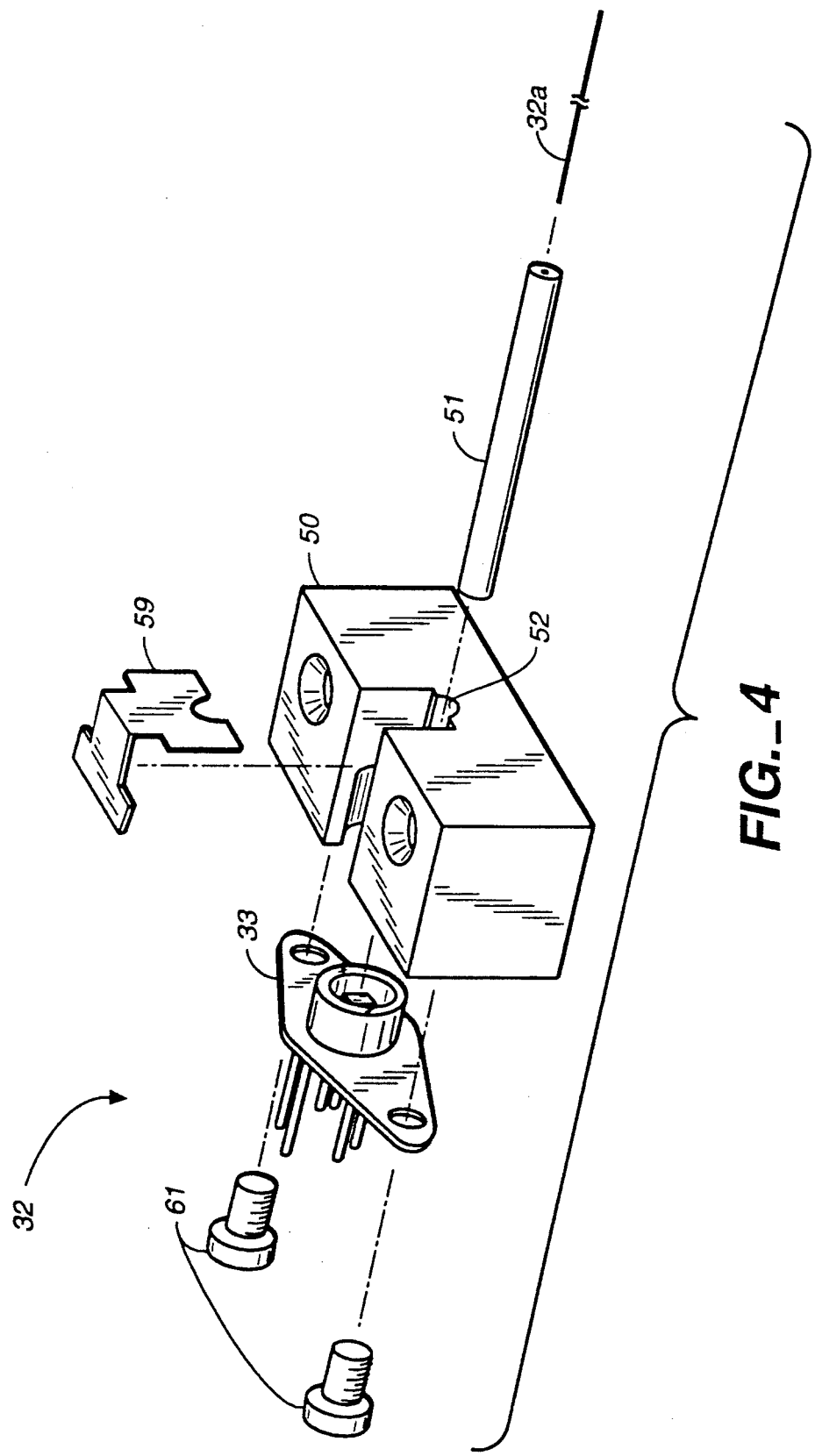
FIG._4

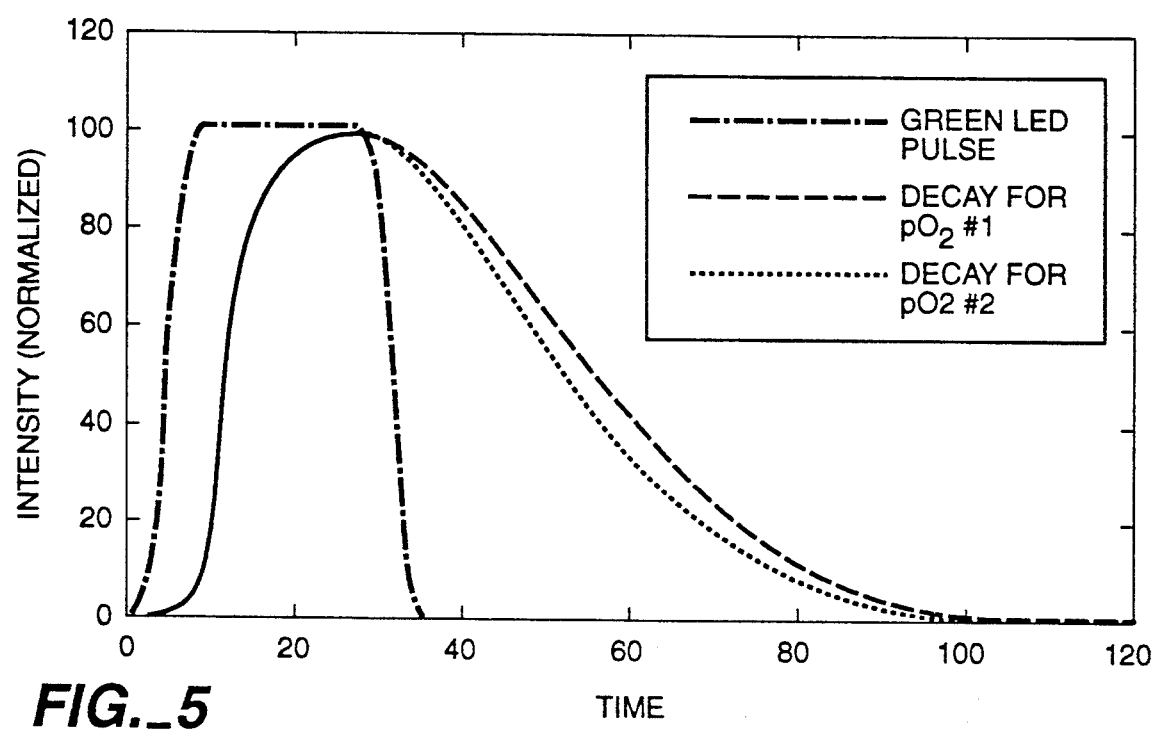
FIG._5

OPTICAL FIBER DISTRIBUTION SYSTEM FOR AN OPTICAL FIBER SENSOR IN A LUMINESCENT SENSOR SYSTEM

FIELD OF THE INVENTION

This invention relates to an optical fiber distribution system suitable for use in an optical fiber sensor system and, more particularly, for use in an optical fiber sensor system having a sensor tip made up of a single fiber and incorporating optical wavelength sensitive indicators to monitor analyte concentrations in compositions, and having distribution system monitoring capabilities.

RELATED APPLICATIONS

An optical signal distribution system incorporating an improved absorbance based sensor is described in co-pending U.S. application Ser. No. 961,470 filed Oct. 15, 1992 and assigned to the assignee of the subject application.

BACKGROUND OF THE INVENTION

Optical fiber sensors have been developed to detect the presence and monitor the concentration of various analytes, including oxygen, carbon dioxide, glucose, inorganic ions, and hydrogen ions, in liquids and in gases. Such sensors are based on the recognized phenomenon that the absorbance or luminescence of certain indicator molecules is specifically perturbed in the presence of certain analytes. The perturbation in the absorbance and/or luminescence profile can be detected by monitoring radiation that is reflected or emitted by the indicator molecule when it is in the presence of a specific analyte. The targeted analyte is generally a part of a solution containing a variety of analytes.

Duofiber optical sensors have been developed that position an analyte-sensitive indicator molecule in the light path of a sensor tip. The indicator molecule is typically housed in a sealed chamber whose walls are permeable to the analyte. The sealed chamber is submerged in the analyte-containing solution. The sensor tip includes a pair of optical fibers. The term "duofiber" refers to the number of fibers in the sensor tip. In a duofiber sensor, one fiber transmits electromagnetic radiation, termed measuring signal, from a signal-generating component to the indicator molecule. The other fiber transmits the reflected or emitted light, termed indicator signal, from the sensor tip to a signal-measuring component that measures the indicator signal intensity. The configuration of the optical fibers between the signal-generating component, the sensor tip, and the signal-measuring component describes the optical fiber distribution system for the sensor system.

Although there are two common types of sensor systems: absorption and luminescent, the present invention is used in conjunction with a luminescent system. There are two types of luminescent sensor systems: phosphorescent and fluorescent. Such systems operate on the concept of measuring the luminescent intensity or lifetime of the radiation emitted by the excitation of the analyte-sensitive molecule. The signal generating component irradiates the indicator molecule with light at a wavelength band corresponding to a region of analyte-dependent absorbance by the indicator molecule. Luminescent emission from the indicator molecule is then measured by the signal-measuring component. The ambient analyte concentration is determined by known techniques as a function of the measured luminescent emission.

The optical fiber distribution system is an integral part of the optical fiber luminescent sensor system. The distribution system is made up of optical fibers, connectors, and components. The distribution system directs the measuring signal from the signal-generating component to the sensor tip and also directs the emitted indicator signal from the sensor tip to the signal-measuring component. In a sensor using a luminescent monitoring technique, the analyte concentration is determined by analyzing the emitted indicator signal over a specified time period.

The efficiency and reliability of a sensor system largely depends on its optical fiber distribution system. Although current optical fiber technology may not provide a one hundred percent signal transfer at fiber connection points, the signal reduction at optical fiber connections should be ascertainable and controllable. Variability in analyte concentration measurements that may be related to the optical fiber distribution system arise from fiber loss, fiber coupling inefficiency, fiber concentration, and response to noise, either random or periodic, produced by a variety of internal and external sources.

In current medical applications, it is desirable that the fiber distribution system be relatively small, flexible, and highly efficient. The size requirement becomes more crucial as in situ blood gas monitoring techniques are developed. For example, a blood gas catheter or sensor may be inserted into and left in a patient's body for a long period of time to provide continuous monitoring of specific conditions. The catheter tip includes the analyte-sensitive indicator molecule. For the patient's comfort, the catheter tip should be as small as possible. To accommodate this desirable size characteristic, a single fiber extending to the catheter tip is desirable. The remainder of the distribution system is then sized in proportion to the catheter tip fiber for maximum efficiency.

In a single-fiber sensor system, a single optical fiber carries the measuring signal to the indicator molecule, as well as carries the emitted indicator signal from the indicator molecule. One useful characteristic of a single-fiber system is that it is reducible to nearly one-half the size of the duofiber system at the sensor tip. However, a single-fiber sensor presents problems related to the small amount of light a single fiber, as well as the related distribution system, can carry, and the ability of the system to distinguish indicator signals from measuring signals that are reflected at imperfect fiber connections. The former problem is especially prevalent in analog-based sensors. Medical sensors are generally of this type. In analog-based sensors, the intensity of the signal produced at the sensor rather than the mere existence of the signal, as in a digital system, is significant. Each change in signal intensity that is not traceable to a constant in the distribution system will be attributed to a parameter in the monitoring process. Thus, the optical fiber distribution system must be highly predictable and reliable in order to provide useful monitoring results.

One known distribution system for a single-fiber sensor system includes lengths of optical fiber, a dividing connector, a mixing connector, a transmitting connector and a tip connector. The optical fiber lengths are of first and second diameters, the second diameter being larger than the first diameter and being substantially equal to the diameter of the sensor tip fiber. The dividing connector connects at least three intermediate fibers of the first diameter to the signal-generating component to thereby receive intermediate signals. The mixing connector connects a mixing fiber of the second diameter to the intermediate fibers to thereby receive the intermediate signals and blend them into a single mixed signal. The transmitting connector connects a transmitting fiber of the first diameter to the mixing fiber to thereby receive a portion of the mixed signal. The tip connector connects the transmitting fiber to the sensor tip fiber to thereby transmit the mixed signal to the sensor tip, and connects an indicator fiber of the first diameter to the sensor tip to thereby transmit a portion of the resulting indicator signal returned from the sensor tip to the signal-measuring component.

Previous $PO_2$ modules used microfilters, non-cooled L.E.D.'s and a 2×2 optical coupler combination. Because of the small amount of phosphorescent return signal, the previous system provided a level of directivity (or cross-talk) that resulted in minimal performance. The major disadvantages were: low power output from the L.E.D.; poor signal-to-noise values; and a large amount of L.E.D. light corrupting the small amount of sensor phosphorescent return signal.

SUMMARY OF THE INVENTION

Accordingly, an improved sensor system has been devised wherein is provided an optical measuring system that is used to generate continuously a single, pulsed and temperature stabilized wavelength of light, directed into a fiber optic distribution system that illuminates a fiber optic sensor, and measures phosphorescent light that is returned from the sensor. The phosphorescence is analyzed in a time decay mode. The system is packaged in a self-contained module that can be mounted onto a printed circuit board (PCB) for operation. An input signal source, an output signal detector, a signal separator, and a plurality of microfilter components are combined in a unique configuration used for the proposed measurement technique.

In the improved system, spectral band pass microfilters are combined with the signal separator in a unique method to increase performance as it relates to transmission and rejection. The method further combines a pulsed, cooled signal source with the output signal detector to measure a time decay signal, and thereby to deduce the apparent lifetime of the decay. The improved module provides better signal-to-noise performance, allows module fabrication and miniaturization for the product and provides higher, i.e., improved, isolation between the input signal source and the output signal detector, in terms of optical cross-talk. Also, the improved system provides a $PO_2$ channel optical module comprising an input signal source that is thermally stabilized by being mounted on a thermal electric cooler. Additional components include an output signal detector and a preamplifier for the output signal detector.

A phosphorescence decay method as used to determine the sensor response to $PO_2$. The optical distribution system uses a single fiber to route the input signal source to the sensor and to return light from the sensor to the output signal detector. Because of the low efficiency of the sensor, a high level of cross-talk rejection is required, which is accomplished by the use of two discrete spectral interference microfilters and the signal separator.

The optical distribution system filters out undesired wavelengths from the input signal source, routes the desired wavelengths to the sensor, routes the return sensor phosphorescent red signal output light to the output signal detector and enhances the directivity of the measuring system by reducing the contribution of the cross-talk components from the signal generating element to the total signal detected by the output signal detector.

Because the signal source of the preferred embodiment of the present invention incorporates a light emitting diode which, like all light sources, changes its wavelength and output power with temperature, the improved distribution system of the present invention incorporates therein a temperature control mechanism for the input signal source.

The improved system provides better signal to noise performance. Additionally, a larger amount of the output from the input signal source is coupled to the actual sensor material, thereby achieving a significantly improved transmission of the control input signal wavelength. Further, the proposed system provides improved isolation between the input signal source and the output signal detector, in terms of optical cross-talk.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a block diagram of an optical detection system for a luminescent sensor, including an optical fiber distribution system in accordance with the invention;

FIG. 2 is a schematic diagram in block form of the improved fiber optic distribution system of the present invention;

FIG. 3 is a schematic representation of the improved LED configuration incorporating a temperature stabilization component;

FIG. 4 is an exploded perspective view of the LED assembly; and

FIG. 5 is a graph of the phosphorescence decay method used to determine sensor response to $PO_2$.

DESCRIPTION OF THE PREFERRED EMBODIMENTS

The optical fiber distribution system of the present invention is suitable for use in conjunction with a variety of physiological pH and blood gas concentration sensors. The distribution system is integratable into a single-fiber tip sensor system. Preferred embodiments of the distribution system will be described in conjunction with $PO_2$ luminescent sensors. However, it is to be understood that the following descriptions are not meant to limit the present invention for use in conjunction with any specific sensor types.

FIG. 1 shows a representative sensor system 30 for determining the $PO_2$ concentration of gaseous compositions by measuring the quenching of various sensor indicator molecules by the composition. FIG. 1 is similar to FIG. 1 of U.S. Pat. No. 4,907,857 entitled "Optical Fiber Distribution System for an Optical Fiber Sensor" issued Mar. 13, 1990 and assigned to the assignee of the present invention ("the '857 Patent"). To the extent that an understanding of the optical fiber distribution system of the above noted patent is useful to an understanding of the present invention, the above noted U.S. Patent is herein incorporated by reference.

The sensor system 30 includes: thermally cooled signal-generating component 32; optical distribution system 36; sensor tip 37; signal-measuring subsystem 38; and microcomputer 40. The signal-measuring subsystem 38 includes: an output signal detector 42; a signal preamplifier 44; and a signal converter 46.

The system 30 provides light excitation of a $PO_2$ luminescent-sensitive composition 48, such as a porphyrin based composition, sequestered in the sensor tip 37. The sensor tip 37 and composition 48 are submerged in an analyte-containing solution (not shown). The signal transmitted from thermally cooled signal-generating component 32, preferably a single colored LED, passes through optical fiber distribution system 36. LED signal-generating component 32 generates a signal, termed measuring signal that energizes the indicator molecule. Another form of optical component, such as a laser, can be used as a signal source 32 for the input signal. The indicator molecule emits light of a different wavelength in proportion to the presence of $PO_2$ in the analyte-containing solution.

In a phosphorescent monitoring system, only a single signal source is required. The phosphorescence is an inherent quality of the sensor that is fixed by the dye matrix. The decay time for any given $PO_2$ quantity is unique. Thus, the intensity of the measured or indicator signal does not affect the measuring process. Thus, unlike an absorbance based sensor system, no reference signal is necessary to monitor distribution system operation to guard against unexpected signal intensity reduction due to distribution system malfunctions.

The radiation in the measuring signal excites the indicator molecule in proportion to the quantity of the analyte present in the analyte-containing solution. At the sensor tip, the excitation caused by the measuring signal causes the luminescent-sensitive composition to emit radiation, identified as a response signal. The response signal includes radiation in a wavelength band corresponding to the emission caused by the measuring signal. The signal detector 42 includes a wavelength-isolation component to isolate the emitted radiation. An example of a wavelength isolation component is a spectral filter that isolates the spectral region of interest. The distribution system transmits the response signal from the sensor tip to the signal detector 42.

The output signal detector 42 receives optical signals as input and outputs corresponding electrical signals. An example of a conventional signal detector is a PIN (p*material-intrinsic material-n*material) silicon component. However, in the preferred embodiment a high gain avalanche photodiode (APD) 42 is used as the output signal detector. The response signal is transmitted to preamplifier 44. The preamplifier 44 transmits the amplified signal to the signal converter 46, which converts the signal from a time decay analog signal to a digital signal. The signal is then input into the microcomputer 40, which monitors the sensor's operation and acts as an input/output device for the sensor.

The microcomputer 40 analyzes the signals received from the signal-measuring component 38 to monitor the presence of the analyte as well as the distribution system operation. In the microcomputer, the time decay of the emitted signal in the wavelength band corresponding to the excitation caused by the measuring signal is measured. One method of measuring the time decay of the signal is to consider a division of the signal as a function of time and compare the ratio of the two parts as a function of time. This comparison produces an indication of the presence of the analyte in the solution being monitored.

The sensor system 30 transmits the measuring signal to the sensor tip 37. At the sensor tip 37, the measuring signal encounters the analyte-sensitive composition. FIG. 2 is a schematic diagram of the optical distribution system 36 of the present invention. The $PO_2$ channel optical module 36 is a one LED system including a thermally cooled LED input signal source 32 which is thermally stabilized by being mounted on a thermal electric cooler 56 as better seen in FIGS. 3 and 4 and described in detail below.

The module includes a wavelength selective optical distribution system consisting of a pair of spectral microfilters 45 and 47, the filter 45 being a green pass filter, and the filter 47 being a red pass filter. The wavelength selective distribution system also includes a signal separator 49. In the preferred embodiment, a Wavelength Division Multiplexer produced by Kaptron Inc. is employed as the signal separator 49. However, other wavelength division multiplexers are available for use in the optical sensor 36 of the present invention. Input optical fiber 32a connects LED signal source 32 to the signal separator 49. The optical distribution system 36 also includes an output signal detector 42, which comprises a high gain avalanche photodiode APD. However, the APD 42 of the present invention could be replaced by a comparable signal detector, such as a PIN device. Output optical fiber 42a connects the WDM signal separator 49 to the APD signal detector 42. Connector tip fiber 58 connects the sensor 37 to the WDM signal separator 49. All of the electro-optical components are solid state devices, chosen to provide long operational lifetimes. The module 36 is self-contained, and can be directly mounted onto a printed circuit board (not shown).

The thermally cooled LED signal source assembly 32, shown in greater detail in FIGS. 3 and 4, includes an LED signal source 33 which, like all light sources, changes wavelength and output power with temperature. The efficiency of the sensor changes with wavelength. In order to insure proper sensor operation, the temperature of the LED signal source must be controlled. The LED signal source assembly 32 comprises a mounting block or thermal block 50 having supported therein an input optical fiber 32a. The fiber 32a is received in a positioning tube 51 mounted in a groove 52 provided in the mounting block 50. While it is desirable to use a single positioning tube 51 to receive and hold the optical fiber 32a, it is also possible to receive and hold optical fiber 58 with a series of concentric tubes similarly positioned as the tube 51 in FIGS. 3 and 4. The LED signal source assembly 32 is shown mounted in a cavity 54 of the mounting block 50 with the LED signal source assembly 32 further including a thermal electric cooler 56, an LED chip 57 and an LED lens 58.

To accomplish temperature control and insure proper sensor operation, the thermal electric cooler (TEC) 56 maintains the temperature of the LED chip 57 near 20 degrees. While fiber optic systems for telecommunications and aerospace applications use light sources in the infrared range of the spectrum (800 nanometers to 1300 nanometers), with power outputs in the milliwatt range, the sensor of the present invention requires a visible light LED. Since visible light LEDs are not optimized in terms of power output for fiber optic use, the lens 58 can be added to the LED package to increase the coupling efficiency of the emitted light into the optical fiber 32a. While conventional optics theory would predict higher efficiency for an optical cooling mechanism which incorporates a lens, actual implementation did not meet theoretical predictions, and the preferred cooling mechanism of the present invention omits the lens 58.

As better seen in FIG. 4, the pigtailed LED assembly 32 is mounted in the aluminum mounting block 50 for both conducting heat away and for removing ambient light. In the preferred embodiment, the optical fiber 32a is mounted within a metal sleeve 51 to align the optical fiber 32a in the groove 52 of the metal block 50. Brass alignment tube 51 receives the optical fiber 32a. The tube 51 is then glued into the groove 52 in the mounting block 50.

Overlying the LED signal source assembly 32 a dust cap 59 serves as a dust cover and blocks ambient light. The LED signal source 33 is mounted to the back of the block 50 by screws 61. The optical fiber 32a is mounted within the metal sleeve 51 and positioned in front of the LED chip 57 to provide an air gap therebetween to obtain maximum coupling efficiency while minimizing mechanical motion effects. Although the lens 58 is omitted in the preferred embodiment, an air gap is provided between the LED chip surface and the fiber end to reduce any effects due to temperature variations between the two components.

In the present invention, the distribution system as connected to a sensor tip in a luminescent sensor system. In a luminescent sensor system, the wavelength of the emitted signal is of a different wavelength than the measuring signal used to excite the indicator molecule. To monitor the presence of the analyte, the input and output signals are isolated by filtering, and the time decay of the emitted signal is measured.

As shown in FIG. 5, a phosphorescence decay method is used to determine the sensor response to $PO_2$. The sensor 37 is a phosphorous chemical (phorphryn) which absorbs green light and radiates red light. The green light energizes the molecules in the sensor 37, and sensor molecules radiate that energy with red light. The rate at which the sensor molecules radiate the energy is dependent upon the oxygen concentration at the sensor 37. Alternative embodiments include a chemical which would absorb blue light and radiate red light.

In operation, the $PO_2$ sensor system 36 generates green light and routes it to the sensor 37, and receives the returned red light from the sensor 37 and routes it to the signal detector 42 because the system 36 uses a single fiber, a single component must accomplish this routing. The wavelength division multiplexer (WDM) signal separator 49 is a device that works like a prism. Incoming green light from the LED signal source 32 is transferred to the sensor fiber 58. Red light output from the sensor 37 is transferred from the sensor fiber 58 to the APD output signal detector 42. The WDM signal separator 49 separates the green light input and the red light output on the sensor fiber 58 into incoming green light from the LED signal source 32 and output red light to the APD signal detector 42. Another form of the signal separator 49 could be a multiplexer incorporating the microfilters 45 and 47 within the multiplexer structure.

An initial LED input signal pulse is transmitted along the input fiber 32a through the green pass microfilter 45 and transmitted through the WDM signal separator 49 to the sensor 37 along the sensor fiber 58. The sensor fiber 58 routes the LED input (green) light to the sensor 37 and returns output (red) light from the sensor 37 to the APD signal detector 42 via the WDM signal separator 49 and the red pass microfilter 47.

The present sensor system overcomes three major problems. First, the sensor 37 is very inefficient. Second, the green LED signal source 32 cannot get much light into the input optical fiber 32a. Third, the green wavelength of the input or excitation light is close to the wavelength of the output returned light. Because of the low efficiency of the sensor 37, any stray LED (green) light will corrupt the measured red signal, thereby significantly reducing sensor performance. Accordingly, a high level of cross-talk rejection is required.

The first two problems necessitate the use of very sensitive detector electronics. With high gains, any stray input (green) light can completely overwhelm the returned signal (red) light. To solve this problem, the WDM signal separator 49 routes the input (green) light to the sensor 37, routes the return (red) light to the APD signal detector 42, thereby eliminating the input (green) light from getting to the APD signal detector 42. Because the WDM signal separator 49 is not perfect, and because of the small separation between the input (green) and the output (red) spectral peaks, the sensor system 36 includes the two extra microfilters 45, 47. The first microfilter 45 makes sure the LED signal source 32 (green) does not have any red sidebands and the second microfilter 47 eliminates any stray green light from the output (red) signal.

The WDM signal separator 49 of the preferred embodiment of the present invention uses two signal separator elements. Light returning from the sensor fiber 58 first strikes a first signal separator element 49a, which reflects light having the wavelength of one of the colors (green) onto the input (green) fiber end 32a. Light of a second separate wavelength (red), that is not reflected off the first element 49a, travels to the second signal separator element 49b. The returned red light is reflected onto the output fiber end 42a. In this way the WDM signal separator 49 divides the incoming multicolored light on the probe fiber 58 to transmit input (green) light from the LED assembly 32 to the sensor 37, and to transmit output light from the sensor 37 to the APD signal detector 42. In the preferred embodiment, multiplexer 49 incorporates two signal elements 49a and 49b. Alternative configurations of the multiplexer 49 could incorporate only a single signal separator element or a combination of three or more such elements.

The optical distribution system 36 filters out undesired wavelengths (e.g., red side bands) from the LED signal source 32, routes the desirable green input light to the sensor 37, and routes the returning red output light to the APD signal detector 42. The WDM signal separator 49 and microfilters 45, 47 combine to remove any input (green) light mixed with the returned sensor signal (red).

The optical distribution system 36 operates as follows. The LED signal source 32 is pulsed, and the returned light of the sensor 37 is detected by the APD signal detector 42. The APD signal detector electronically integrates the returned light into two time windows and then compares the integrals using a standard ratiometric algorithm in order to determine the change of state for the sensor 37. The $PO_2$ module 36 has a thermistor mounted in thermal contact with the APD signal detector 42 to measure the APD signal detector temperature, thus allowing compensation for temperature effects, and maintaining accurate fixed gain settings for the PO$_2$ channel.

While a 2×2 optical coupler may be used in analyte detection systems which do not incorporate a luminescence sensor, the need to minimize directivity (or cross-talk), which is a major contributor to decreased performance, is necessary in the present system. This necessity occurs because of low power output from the LED signal source, poor signal-to-noise ratios and a large amount of LED light corrupting the small amount of sensor phosphorescence, i.e., the returned signal. Accordingly, the use of discreet spectral interference microfilters in cooperation with a wavelength division multiplexer provides an improved system which produces better signal to noise performance. The improved system provides higher isolation between source and detector in terms of optical cross-talk. Moreover, the compact nature of the system allows the module concept to function within the environment of the product and the module concept facilitates both fabrication and miniaturization of the product.

While preferred embodiments of the invention have been illustrated and described, it will be appreciated that various changes can be made therein without departing from the spirit and scope of the invention. The appended claims more appropriately describe the breadth of the present invention.

The embodiments of the invention in which an exclusive property or privilege is claimed are defined as follows:

1. A distribution system for a sensor that utilizes an analyte-sensitive indicator module to monitor the concentration of an analyte, the sensor having: a temperature stabilized signal generating component for generating a first optical signal of a precise first wavelength, an indicator molecule for producing a second returned optical signal of a precise second wavelength, the first signal wavelength being such that the intensity and temporal behavior of the signal is predictably altered by the indicator molecule so that the wavelength temporal behavior of the returned signal is predictable; a single-fiber sensor tip that includes the indicator molecule; and a signal-measuring compound for receiving signals from the distribution system, the distribution system comprising:

a temperature stabilized, signal generating component for generating said first optical signal of a precise first wavelength;
   a signal detector;
   a signal separating component for delivering said first optical signal of a precise first wavelength to the sensor, delivering said second returned optical signal of a precise second wavelength to said signal detector, and including signal interference means to separate said first and second signals and minimize cross-talk therebetween;
   at least one discrete spectral interference microfilter for eliminating side bands of the wavelength of the second returned optical signal from the first optical signal and at least another discrete spectral interference microfilter for eliminating the wavelength of the first optical signal from the second returned optical signal to the signal detector; and
   a sensor optical fiber for connecting a sensor tip to the signal separating component to transmit said first optical signal to the sensor tip, and to return the resulting indicator signal from the sensor tip to the signal separating component, said
   signal detector receiving said second returned signal from the signal separating component and transmitting it to the signal-measuring component, the signal output is substantially smaller than the signal input and whereby the intensity of said first signal is maximized such that the intensity of the indicator signal of a wavelength corresponding to the wavelength of the signal received by the signal-measuring component is suitable for monitoring the signal input to the distribution system.

2. A distribution system for a sensor as claimed in claim 1 wherein the temperature stabilized signal generating component comprises an LED assembly for generating said first optical signal of a precise first wavelength.

3. A distribution system for a sensor as claimed in claim 1 wherein the temperature stabilized signal generating component comprises a laser for generating said first optical signal of a precise first wavelength.

4. A distribution system for a sensor as claimed in claim 1 wherein the signal separating component comprises a wavelength division multiplexer including a first signal separator element and a second signal separator element, with light returning from the sensor fiber first striking the first signal separator element which reflects the first signal onto a first fiber end associated with the signal indicating component, with the light that is not reflected off of the first signal separator element traveling to the second signal separator element and is reflected onto a second fiber end associated with the signal detector, thus separating the components of incoming multi-colored light and directing each component to a respective filter.

5. A distribution system for a sensor as claimed in claim 1 wherein the signal detector for receiving said second returned optical signal comprises an avalanche photo diode (APD).

6. A distribution system for a sensor as claimed in claim 1 wherein the signal detector for receiving said second returned optical signal comprises a p*material-intrinsic material-n*material (PIN) device.

7. An improved modular optical sensor for decoding phosphorescent base sensor signals where the signal output is substantially smaller than the signal input, said sensor comprising:

a temperature stabilized signal generating component for generating a first optical signal of a precise first wavelength;
   an indicator molecule for producing a second returned signal of a precise second wavelength;
   the first signal wavelength being such that the intensity and temporal behavior of the signal is predictably altered by the indicator molecule so that the wavelength temporal behavior of the returned signal is predictable;
   a single-fiber sensor tip that includes the indicator molecule;
   a signal detector;
   a signal separating component for delivering said first optical signal of a precise first wavelength to the sensor, delivering said second returned optical signal of a precise second wavelength to said signal detector, and including signal interference means to separate said first and second signals and minimize cross-talk therebetween; and at least one discrete spectral interference microfilter for eliminating side bands of the wavelength of the second returned optical signal from the first optical signal and at least one discrete spectral interference microfilter for eliminating wavelengths of the first optical signal from the second returned optical signal to the signal detector; and signal detector receiving said second returned signal, the signal separating component operative to separate said first optical signal from said second returned signal thus to minimize cross-talk and prevent light of the first signal wavelength from entering to the signal detector.

8. An improved optical sensor as claimed in claim 7 wherein the temperature stabilized signal generating component comprises an LED assembly for generating said first optical signal of a precise first wavelength.

9. An improved optical sensor as claimed in claim 7 wherein the temperature stabilized signal generating component comprises a laser for generating said first optical signal of a precise first wavelength.

10. An improved optical sensor as claimed in claim 7 wherein the signal separating component comprises a wavelength division multiplexer including a first signal separator element and a second signal separator element, with light returning from the sensor tip first striking the first signal separator element which reflects the first signal onto a first fiber end associated with the signal indicating component, with the light that is not reflected off of the first signal separator element traveling to the second signal separator element and is reflected onto a second fiber end associated with the signal detector, thus separating the components of incoming multi-colored light and directing each component to a respective fiber.

11. A distribution system for a sensor as claimed in claim 7 wherein the signal detector for receiving said second returned optical signal comprises an avalanche photo diode (APD).

12. A distribution system for a sensor as claimed in claim 7 wherein the signal detector for receiving said second returned optical signal comprises a p*material-intrinsic material-n*material (PIN) device.

13. A distribution system for a sensor that utilizes an analyte-sensitive indicator module to monitor the concentration of an analyte, the sensor having: a signal-generating component for producing a first optical signal of a distinct first wavelength, an indicator molecule for producing a second returned optical signal of a distinct second wavelength, the first signal wavelength being such that the intensity and temporal behavior of the signal is predictably altered by the indicator molecule so that the wavelength temporal behavior of the returned signal is predictable; a single-fiber sensor tip that includes the indicator molecule; and a signal-measuring compound for receiving signals from the distribution system, the distribution system comprising:

a temperature stabilized LED assembly for generating said first optical signal of a precise first wavelength;

an avalanche photodiode output signal detector;

a wavelength division multiplexer for delivering said first optical signal of a precise first wavelength to the sensor, delivering said second returned optical signal of a precise second wavelength to said output signal detector, the wavelength division multiplexer to separate said first and second signals and minimize cross-talk therebetween; said output signal detector for receiving said second return signal from the wavelength division multiplexer and transmitting it to the signal measuring component;

and at least one discrete spectral interface micro filter for eliminating side bands of the wavelength of the second returned optical signal from the first optical signal and at least another discrete spectral interference microfilter for eliminating stray side bands of the wavelength of the first optical signal from the second returned optical signal to the avalanche photo diode, said output signal detector receiving said second returned signal from the signal separating component and transmitting it to the signal-measuring component, the signal output is substantially smaller than the signal input, and whereby the intensity of said first signal is maximized such that the intensity of the indicator signal of a wavelength corresponding to the wavelength of the signal received by the signal-measuring component is suitable for monitoring the signal input to the distribution system.

14. A method to monitor the concentration of an analyte with a sensor that utilizes an analyte-sensitive indicator molecule wherein the signal output of the sensor is substantially smaller than the signal input, the method including the steps of:

producing a first optical signal of a precise first wavelength with a temperature stabilized signal generating component;

producing a second returned optical signal of a precise second wavelength with an indicator molecule;

predictably altering the intensity and temporal behavior of the first signal wavelength with the indicator molecule so that the wavelength and temporal behavior of the returned signal is predictable;

providing a single-fiber sensor tip that includes the indicator molecule; and receiving signals from the distribution system with a signal-measuring component, the method further including the steps of:

generating said first optical signal of a precise first wavelength with a temperature stabilized signal generating component;

providing a signal detector;

delivering said first optical signal of a precise first wavelength to the sensor with a signal separating component, delivering said second returned optical signal of a precise second wavelength to said signal detector, and separating said first and second signals with signal interference means to minimize cross-talk therebetween;

eliminating side bands of the wavelength of the second returned optical signal from the first optical signal with at least one discrete spectral interference microfilter and eliminating the wavelength of the first optical signal from the second returned optical signal to the signal detector with at least another discrete spectral interference microfilter;

connecting a sensor tip to the signal separating component by a sensor optical fiber to transmit said first optical signal to the sensor tip, and returning the resulting indicator signal from the sensor tip to the signal separating component; and receiving said second returned signal from said signal separating component and transmitting it to the signal-measuring component with said signal detector, maximizing the intensity of said first signal of a precise first wavelength such that the intensity of the indicator signal of a wavelength corresponding to the wavelength of the signal received by the signal-measuring component is suitable for monitoring signal input to the distribution system.

* * * * *